US010674988B2

(12) United States Patent
Kim et al.

(10) Patent No.: US 10,674,988 B2
(45) Date of Patent: Jun. 9, 2020

(54) CHARGING CRADLE FOR PROVIDING REAL-TIME INFORMATION, AND PORTABLE RADIOGRAPHY DEVICE INCLUDING SAME

(71) Applicants: VATECH Co., Ltd., Gyeonggi-do (KR); VATECH EWOO Holdings Co., Ltd., Gyeonggi-do (KR)

(72) Inventors: Yeong Kyun Kim, Gyeonggi-do (KR); Tae Woo Kim, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 28 days.

(21) Appl. No.: 16/068,129

(22) PCT Filed: Jan. 4, 2017

(86) PCT No.: PCT/KR2017/000115
§ 371 (c)(1),
(2) Date: Jul. 4, 2018

(87) PCT Pub. No.: WO2017/119724
PCT Pub. Date: Jul. 13, 2017

(65) Prior Publication Data
US 2019/0015066 A1 Jan. 17, 2019

(30) Foreign Application Priority Data
Jan. 5, 2016 (KR) .......................... 10-2016-0000867

(51) Int. Cl.
*A61B 6/00* (2006.01)
*H01M 10/46* (2006.01)
(Continued)

(52) U.S. Cl.
CPC ................ *A61B 6/56* (2013.01); *A61B 6/145* (2013.01); *A61B 6/4405* (2013.01);
(Continued)

(58) Field of Classification Search
CPC ......... A61B 6/145; A61B 6/4405; A61B 6/56; A61B 6/00; A61B 6/40; A61B 6/467;
(Continued)

(56) References Cited

U.S. PATENT DOCUMENTS

| 4,160,266 A * | 7/1979 | Kurihara .................. A61B 6/00 378/117 |
| 2007/0140424 A1* | 6/2007 | Serceki .................. G01N 23/04 378/62 |
| 2008/0312852 A1 | 12/2008 | Maack |

FOREIGN PATENT DOCUMENTS

| JP | 2005-304696 A | 11/2005 |
| JP | 2011-136022 A | 7/2011 |

(Continued)

*Primary Examiner* — Chih-Cheng Kao
(74) *Attorney, Agent, or Firm* — IP Legal Services, LLC (57) ABSTRACT

Disclosed are a charging cradle and a portable radiography device including the same, which is capable of displaying the residual battery capacity when the portable radiography device is being charged and even when not being charged and, more specifically, displaying the possible number of times of radiography in real time by using the residual battery capacity, such that a user can exactly determine when to charge. The portable radiography device includes a radiography device main body having a rechargeable battery, a first communication unit provided in the main body to transmit battery charging state information, a charging cradle configured to receive external power to supply charging power to the battery, a second communication unit provided in the charging cradle to receive the battery charging state information from the first communication unit, and
(Continued)

a display unit provided in the charging cradle to display the battery charging state information.

9 Claims, 5 Drawing Sheets

(51) Int. Cl.
  *H01M 2/10*   (2006.01)
  *H01M 10/42*   (2006.01)
  *H01M 10/48*   (2006.01)
  *A61B 6/14*   (2006.01)
(52) U.S. Cl.
  CPC ....... *H01M 2/1022* (2013.01); *H01M 10/425* (2013.01); *H01M 10/46* (2013.01); *H01M 10/48* (2013.01); *H01M 10/488* (2013.01); *A61B 6/40* (2013.01); *A61B 6/467* (2013.01); *A61B 6/54* (2013.01); *H01M 2010/4271* (2013.01); *H01M 2010/4278* (2013.01)
(58) Field of Classification Search
  CPC .... H01M 10/425; H01M 10/46; H01M 10/48; H01M 2010/4271; H01M 2010/4278; H01M 2/1022; H01M 10/488
  See application file for complete search history.

(56) References Cited

FOREIGN PATENT DOCUMENTS

| | | |
|---|---|---|
| JP | 2012-161614 A | 8/2012 |
| JP | 5390746 B2 | 1/2014 |
| KR | 10-2007-0118369 A | 12/2007 |

\* cited by examiner

CHARGING CRADLE FOR PROVIDING REAL-TIME INFORMATION, AND PORTABLE RADIOGRAPHY DEVICE INCLUDING SAME

CROSS REFERENCE TO RELATED APPLICATIONS

This application is a National Stage Patent Application of PCT International Patent Application No. PCT/KR2017/000115 (filed on Jan. 4, 2017) under 35 U.S.C. § 371, which claims priority to Korean Patent Application No. 10-2016-0000867 (filed on Jan. 5, 2016), the teachings of which are incorporated herein in their entireties by reference.

TECHNICAL FIELD

The present invention relates generally to a portable radiography device. More particularly, the present invention relates to a portable radiography device miniaturized to be suitable for intraoral radiography and the like in dental clinics, and a charging cradle including the same.

BACKGROUND ART

X-ray imaging is a radiography method using straightness and attenuation of X-rays, and based on the amount of attenuation accumulated in the course of the X-rays passing through an imaging area, it provides an X-ray image of the internal structure of the imaging area. To achieve this, an X-ray imaging system includes: an X-ray generation apparatus configured to irradiate X-rays to a imaging area; an X-ray sensor disposed to face the X-ray generation apparatus with the imaging area therebetween, and configured to detect X-rays that have penetrated through the imaging area; and an image processing apparatus configured to construct a gray-level X-ray image of an internal structure of the imaging area by using X-ray projection data, as a detection result detected by the X-ray sensor.

In recent years, X-ray imaging has been rapidly evolving into DR (Digital Radiography) using digital sensors due to the development of semiconductor and information processing technologies, whereby image processing technology has also been developed and is used in various ways according to the purpose and application field. As an example, there is intra-oral X-ray imaging mainly used in dentistry. Intra-oral X-ray imaging is an X-ray imaging technology for obtaining an X-ray image of a limited imaging area of a subject, and is performed as follows: an X-ray sensor is placed inside the subject's mouth; and X-rays are irradiated from an X-ray generation apparatus outside the mouth to the X-ray sensor, thereby obtaining an X-ray image of a tooth and surrounding tissue that is disposed between the X-ray generation apparatus and the X-ray sensor. The intra-oral X-ray image has advantages of low distortion, excellent resolution and sharpness, and relatively low radiation exposure, so it is mainly used for implant treatment or endodontic treatment requiring high resolution.

A portable radiography device can utilize battery power to facilitate ease of use. Recently, the development of technology for rechargeable battery such as lithium-ion battery has led to the weight reduction of a high capacity battery. In order to charge the rechargeable battery, a charger is required. In many cases, a charging cradle serving also as a cradle of a portable device is provided along with the portable device. Although the charging cradle is placed in a close and prominent position such as on a device user's desk, the function of the charging cradle is limited to indication of the charging state by the LED color or on and off state of the LED, other than the above-mentioned cradle function. The residual battery capacity and the available time of the battery or the possible number of times of use cannot be exactly predicted before the device is completely discharged and becomes inoperative or fully charged, resulting in inconveniences such as interruption during use.

DISCLOSURE

Technical Problem

Accordingly, the present invention has been proposed to solve the above problems occurring in the related art, and one object of the present invention is to provide a charging cradle and a portable radiography device including the same, which is capable of displaying the residual battery capacity when the portable radiography device is being charged and even when not being charged and, more specifically, displaying the possible number of times of radiography in real time by using the residual battery capacity, such that a user can exactly determine when to charge.

Further, another object of the present invention is to provide a charging cradle and a portable radiography device including the same, which is capable of controlling the charging of the portable device with various charging modes according to setting input of the charging amount based on electric energy, the battery charging ratio, the charging time, the number of times of radiography, or the battery temperature upper limit.

Technical Solution

In order to achieve the above object, according to some aspects of the present invention, there is provided a portable radiography device including: a radiography device main body having a rechargeable battery; a first communication unit provided in the main body, and configured to transmit battery charging state information; a charging cradle configured to receive external power to supply charging power to the battery; a second communication unit provided in the charging cradle, and configured to receive the battery charging state information from the first communication unit; and a display unit provided in the charging cradle, and configured to display the battery charging state information.

The battery charging state information may include information on a possible number of times of radiography according to residual battery capacity. In this case, the portable radiography device may further include a controller provided in at least one of the main body, and the charging cradle, and configured to calculate a real-time possible number of times of radiography by using real-time residual battery capacity detected in a predetermined time period and data on power consumption per one radiography prestored in a memory and provide the real-time possible number of times of radiography to at least one of the first communication unit, and the second communication unit.

Herein, the portable radiography device may further include an input unit provided in at least one of the main body, and the charging cradle, and configured to receive a radiographic mode setting input, wherein the controller calculates a real-time possible number of times of radiography corresponding to a radiographic mode set by input, by using data on power consumption per one radiography by radiographic mode stored in the memory. Further, the predetermined time period may be a time period shorter than a time required to charge the power consumption per one radiography.

Meanwhile, the battery charging state information may include a charging amount based on electric energy, charging ratio with respect to battery capacity, a charging time, or battery temperature information. In this case, the portable radiography device may further include: an input unit provided in at least one of the main body, and the charging cradle, and configured to receive a charging mode setting input; and a controller provided in at least one of the main body, and the charging cradle, and configured to update battery charging state information corresponding to a charging mode set by input in a predetermined time period and provide the same.

Meanwhile, either the first communication unit or the second communication unit may be provided with a beacon communication module, and provides the charging state information or positional information of the main body to a registered mobile device within a beacon communication area provided by the beacon communication module. In this case, the main body may receive radiography information from the registered mobile device within a beacon communication area and set a radiographic mode automatically.

Advantageous Effects

According to the present invention, there is provided a charging cradle and a portable radiography device including the same, which is capable of displaying the residual battery capacity when the portable radiography device is being charged and even not being charged and, more specifically, displaying the possible number of times of radiography in real time by using the residual battery capacity, such that a user can exactly determine when to charge.

According to the present invention, there is further provided a charging cradle and a portable radiography device including the same, which is capable of controlling the charging of the portable device with various charging modes according to setting input of the charging amount based on electric energy, the battery charging ratio, the charging time, the number of times of radiography, or the battery temperature upper limit.

MODE FOR INVENTION

Hereinafter, various embodiments of the present invention will be described with reference to the accompanying drawings. The technical idea of the present invention will be understood more clearly by the embodiments. The present invention is not limited to the embodiments described hereinbelow. The same reference numerals are used to designate the same or similar components, and a description of components having the same reference numerals as those described in any one of the drawings may be omitted.

Figure 1:
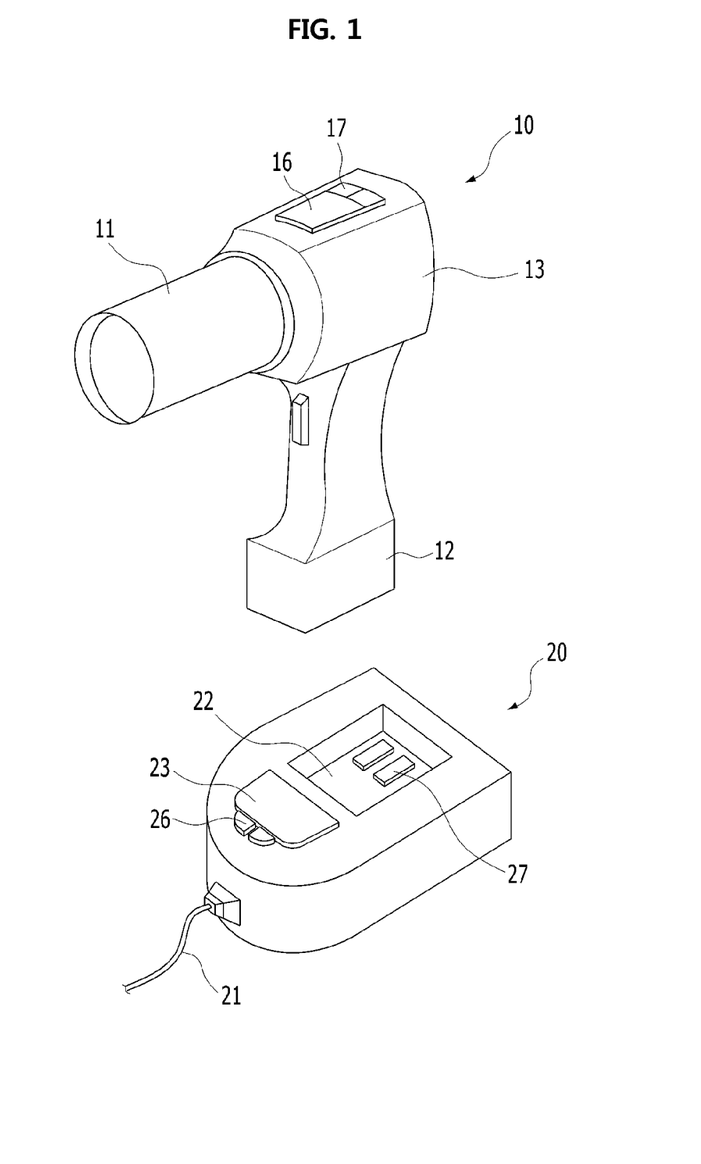
FIG. 1 roughly shows an external configuration of a portable radiography device main body and a charging cradle according to an embodiment of the present invention.
Figure 2:
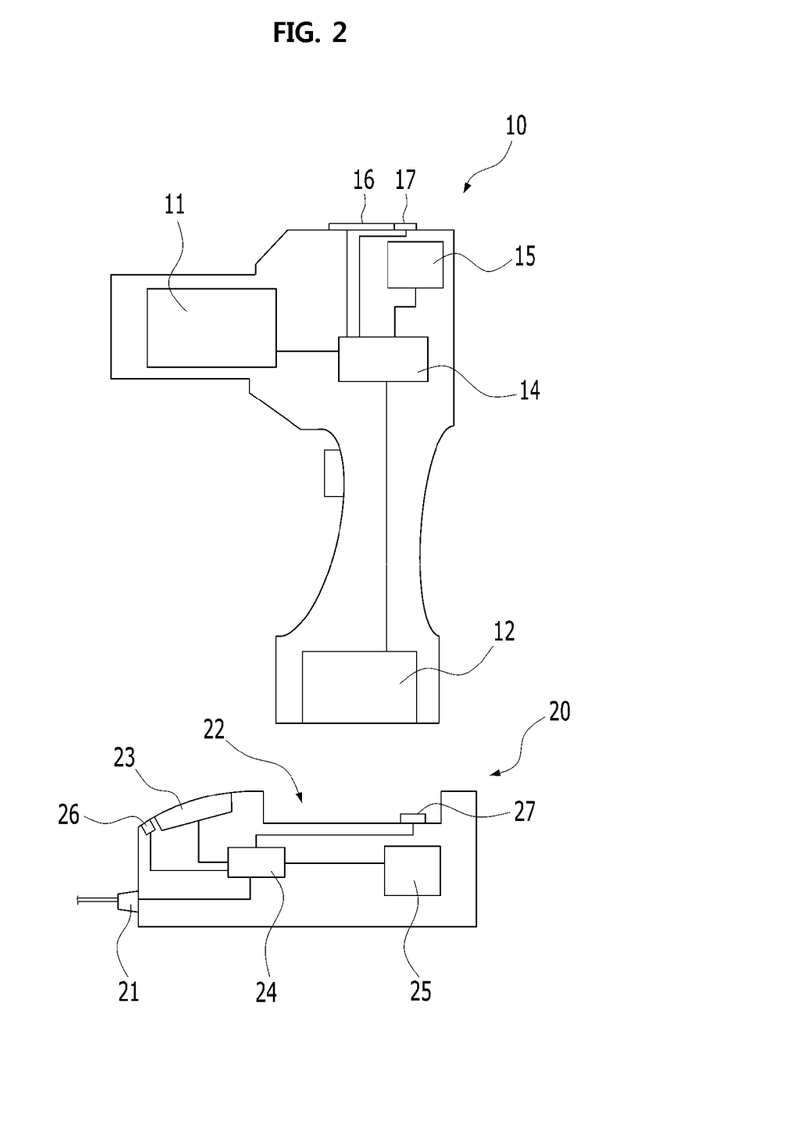
FIG. 2 roughly shows an internal configuration of the portable radiography device main body and the charging cradle according to an embodiment of the present invention.

FIG. 1 roughly shows an external configuration of a portable radiography device main body and a charging cradle according to an embodiment of the present invention; and FIG. 2 roughly shows an internal configuration of the portable radiography device main body and the charging cradle according to an embodiment of the present invention.

A portable radiography device according to the present invention includes a portable radiography device main body 10, and a charging cradle 20. The portable radiography device main body 10 (hereinafter, referred to as a main body) includes: a rechargeable battery 12 for power supply; an X-ray source 11 for generating X-rays using power; and a body part 13 provided therein with a first controller 14 for controlling the battery and the X-ray source. The body part 13 may be provided at a side thereof with a first display unit 16 for displaying a user's setting and operating state of the main body 10; and the body part 13 may be provided at a side thereof with a first input unit 17 for inputting the user's setting. The first display unit 16 and the first input unit 17 may be, for example, integrally provided with a touch screen interface.

The first controller 14 uses the power supplied from the battery 12 to provide a control signal such that the X-ray source 11 emits an appropriate amount of X-rays in accordance with the set radiographic mode. The radiographic mode is set differently according to the user's input on the type of tooth to be imaged, for example, whether the subject is an adult or a child, and whether the tooth is a molar, canine, or anterior tooth. The intensity or time of the X-rays emitted from the X-ray source 11 are determined differently according to the radiographic mode.

The main body 10 is provided with a first communication unit 15. The first communication unit 15 can transmit charging state information generated by using the information on the residual battery capacity detected from the battery 12 by the controller 14 or the electric energy supplied to the battery. To be more specific, the first communication unit 15 may include a near field communication module for wirelessly transmitting the charging state information described above. Meanwhile, although not shown here, an X-ray sensor may be wired or wirelessly connected to the main body 10. The X-ray sensor provides an image data by receiving X-rays emitted from the X-ray source 11 and attenuated while transmitted through a subject. When the X-ray sensor is wired or wirelessly connected to the main body 10, the first communication unit 15 can receive the image data and transmit the same, or receive the image data and transmit processed data to the outside.

The charging cradle 20 is provided with a main body mounting portion 22 to which a portion of the main body 10, particularly, the battery 12 portion is accommodated and mounted. The main body mounting portion 22 may be provided with a charging voltage output terminal 27 connected to an input terminal of the battery 12 mounted to the mounting portion. However, when the wireless charging method is adopted, the charging voltage output terminal 27 may be omitted.

A second display unit 23 as an information display window and a second input unit 26 as an input means for charging setting or display setting are provided outside the charging cradle 20. Of course, they can be integrated into a touch screen interface. The charging cradle 20 may be provided therein with a power input unit 21 with external power input thereinto, and a second controller 24 electrically connected to the second display unit 23, the second input unit 26, and the charging voltage output terminal 27 described above. Further, the charging cradle 20 is provided with a second communication unit 25 connected with the second controller 24. The second communication unit 25 may be connected, for example, to the above described first communication unit 15 to transmit and receive charging mode setting information, charging state information, and the like.

The charging state information may include information on a possible number of times of radiography according to residual battery capacity. Further, the charging state information may include a charging amount based on electric energy, charging ratio with respect to battery capacity, a charging time, or battery temperature information. The charging state information displayed on the second display unit 23 may vary depending on the charging mode set by the user input via the first input unit 17 or the second input unit 26. For example, the user can select a mode for charging, as an example of the charging mode, in which it is possible to perform radiography the desired number of times. In this case, the possible number of times of radiography according to the residual battery capacity charged in the battery 12 may be displayed on the second display unit 23 in real time. Even when there is no separate charging mode input, it is possible to display the possible number of times of radiography in real time. The user can select a mode for charging, as another example of the charging mode, in which it is possible to charge the battery up to the predetermined charging amount based on electric energy. In this case, the charging amount based on electric energy or the charging ratio with respect to battery capacity may be displayed on the second display unit 23 in real time. Other than this, when the user selects a charging mode that sets the charging time or the battery temperature upper limit, the elapsed charging time or the battery temperature may be displayed. Meanwhile, two or more of a variety of the battery state information described above may be simultaneously displayed on the second display unit 23.

To display the battery state information described above, the second controller 24 can transmit and receive the necessary information with the first controller 14 of the main body 10 through the second communication unit 25 and the first communication unit 15. For example, the second controller 24 may provide information about charging mode or radiographic mode settings input via the second input unit 26 and information about the power supplied from the power input unit 21 to the charging voltage output terminal 27, and may be provided with real-time charging state information calculated from the first controller 14 such that the information is displayed on the second display unit 23.

Herein, the real-time charging state information refers to the real-time charging state information at a level that is updated in a predetermined time period and is informed to the user when a meaningful change in charging progress occurs. For example, when the real-time possible number of times of radiography is displayed on the second display unit 23, it is preferred that the predetermined time period be a time period shorter than a time required to charge the power consumption per one radiography.

Meanwhile, either the first communication unit 15 or the second communication unit 25 may be provided with a beacon communication module. The beacon communication module can sense that a pre-registered mobile device enters a predetermined near field communication area, for example, a hospital with a radiography device disposed therein, and transmit the above-described charging state information, the set charging mode, the set radiographic mode, or the like to the mobile device while being in the area. The transmission of this information may be performed directly between the beacon communication module and the registered mobile device, or indirectly via the wireless communication network to which the mobile device is connected. Herein, the registered mobile device may be, for example, a mobile device of the radiography staff. Further, the beacon communication module may transmit positional information of the radiography device main body 10 to the mobile device, such that the radiography staff can easily identify the position of the device main body.

Further, the radiography device main body 10 may receive personal information such as the age and physique of the subject, or radiography information such as a target area, other radiography conditions, or the like, from the mobile device connected through the beacon communication module, and may automatically reflect the received radiography information onto the radiographic mode selection.

Hereinbelow, as an example of the real-time charging state information described above, the configuration and the operation of displaying the possible number of times of radiography on the display unit of the charging cradle will be described.

Figure 3:
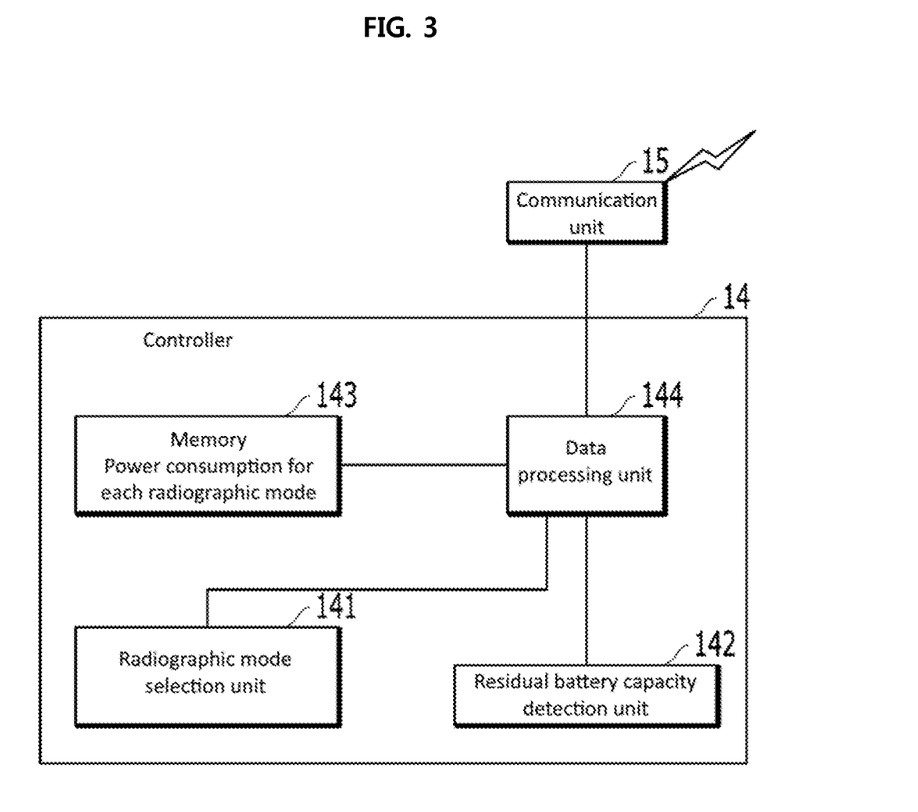
FIG. 3 shows a configuration of a controller of the portable radiography device main body according to an embodiment of the present invention.

FIG. 3 shows a configuration of a controller of the portable radiography device main body according to an embodiment of the present invention.

The first controller 14 of the main body 10 may include: a residual battery capacity detection unit 142 configured to detect electric energy charged in the battery in real time, that is, residual battery capacity, by being connected to the battery; a memory 143 with data on power consumption per one radiography stored therein; and an data processing unit 144 configured to calculate real-time possible number of times of radiography by, for example, dividing real-time residual battery capacity by the power consumption per one radiography. The information calculated by the data processing unit 144 is transmitted to the second communication unit of the charging cradle through the first communication unit 15 as described above.

Further, the first controller 14 may be provided with a radiographic mode/charging mode selection unit 141 for setting a radiographic mode or a charging mode by user input through the first input unit 17 of the main body. In the memory 143, power consumption data according to each radiographic mode is stored in advance, wherein the power consumption data may be stored at the time of device manufacture, or the data based on the actual measured power consumption during use of the device may be stored for each radiographic mode. Meanwhile, the input of the radiographic mode or the charging mode may be input through a second input unit of the charging cradle. In this case, the input information may be transmitted to the first controller 14 via the second communication unit and the first communication unit.

Figure 4:
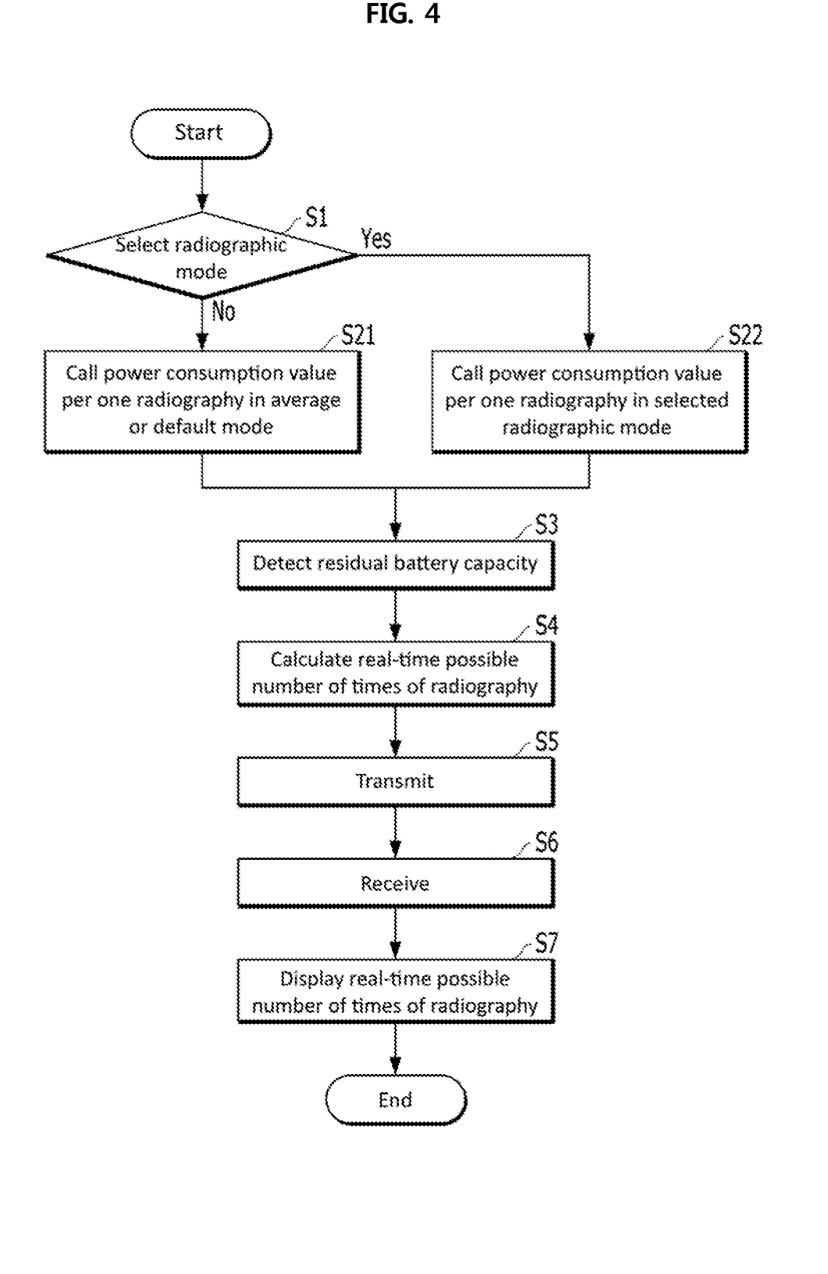
FIG. 4 shows a flow of display function about the real-time possible number of times of radiography performed in a portable radiography device according to an embodiment of the present invention.

FIG. 4 shows a flow of display function about the real-time possible number of times of radiography performed in the portable radiography device according to an embodiment of the present invention.

As shown in the drawing, when the user selects the radiographic mode (S1), the power consumption value per one radiography corresponding to the selected radiographic mode is called from the memory (S22). In the absence of the user's selection of radiographic mode (S1), the average power consumption value per one radiography of various radiographic modes or the power consumption value per one radiography corresponding to the default radiographic mode may be called from the memory (S21). After the residual battery capacity is detected in real time (S3) and the real-time possible number of times of radiography is calculated (S4), the information is transmitted through the first communication unit (S5) and is received by the second communication unit (S6), whereby the real-time possible number of times of radiography is displayed on a second display unit of the charging cradle (S7).

Herein, the operation of detecting the residual battery capacity in real time (S3) may be performed irrespective of the process of selecting the radiographic mode (S1) and calling the power consumption value per one radiography (S21 and S22). For example, the residual battery capacity information detected in a predetermined time period is temporarily stored by assigning an area to the memory, and this information can be used whenever the real-time possible number of times of radiography is calculated (S4).

Meanwhile, the sequence of steps described above may be repeated in a predetermined time period. Further, radiographic mode selection information is stored in the memory, and if there is no change in the value thereof, only the process after detecting residual battery capacity (S3) described above may be repeated.

Figure 5:
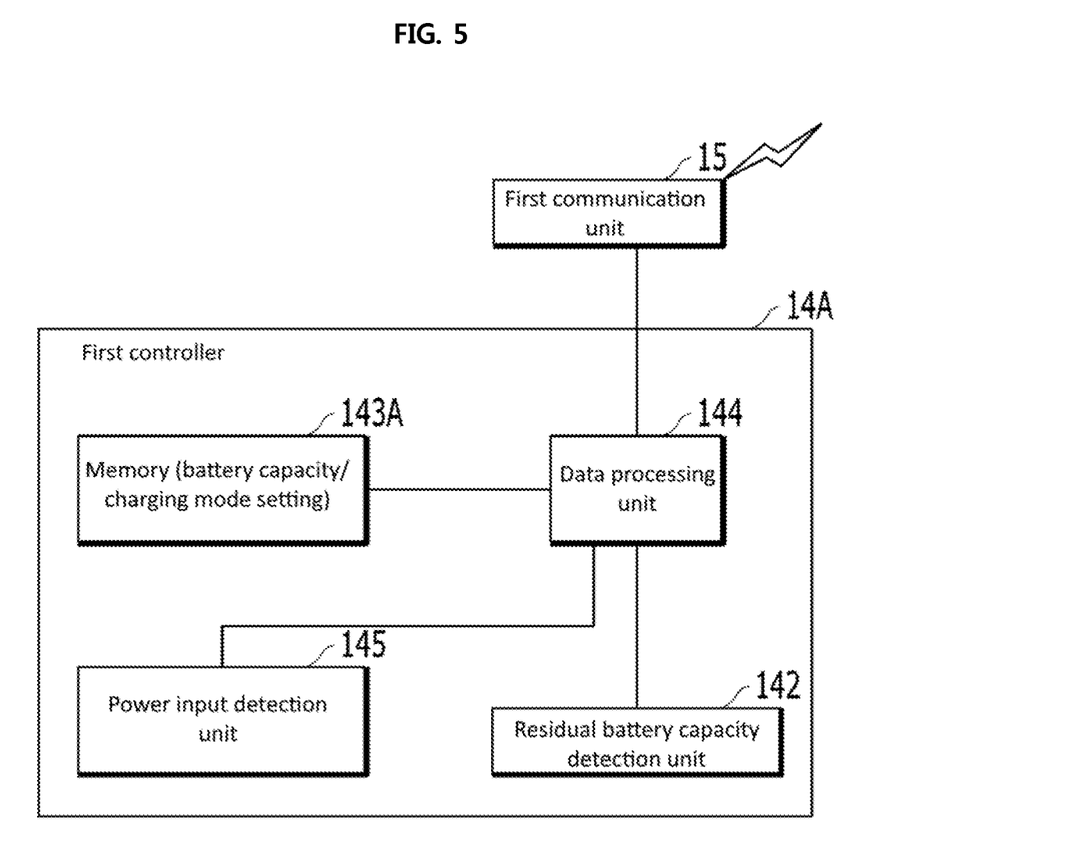
FIG. 5 shows a configuration of a controller of the portable radiography device main body according to an embodiment of the present invention.

FIG. 5 shows a configuration of a controller of the portable radiography device main body according to an embodiment of the present invention.

This embodiment relates to a configuration for receiving charging mode selection information from the user and providing charging state information corresponding to the charging mode through the display unit in real time. For example, the first controller 14A, which is the controller of the main body, may be provided with a power input detection unit 145 for detecting information about a power input supplied from the charging cradle to the battery. In addition, in a memory 143A provided in the first controller 14A, the capacity data of the battery mounted in the main body may be stored in advance. Furthermore, charging mode setting information by user input may also be stored in the memory 143A.

In this case, the first controller 14A calculates the real-time charging state information corresponding to the preselected charging mode using the data processing unit 144. For example, when the user selects a mode for charging up to a predetermined charging amount based on electric energy, the data processing unit 144 may use the power input detection unit 145 to calculate and display the electric energy supplied to the battery from the start of charging to the present, or may use the residual battery capacity detection unit 142 to calculate the residual battery capacity change value from the start of charging to the present and provide the charging amount based on electric energy information to the first communication unit 15. Meanwhile, when the user selects the charging mode along with the charging ratio with respect to battery capacity, the charging ratio information may be provided in real time using the residual battery capacity change value and the battery capacity data stored in the memory 143A.

Meanwhile, in the above description, the controller, the input unit, and the display unit are provided in the radiography device main body and the charging cradle, respectively, but the present invention is not limited thereto. In particular, in the above-described embodiment, the calculation of the charging state information is performed in the controller of the main body, but the present invention is not limited thereto. Since the main body and the charging cradle can freely exchange the information about the charging mode setting and the radiographic mode setting, or the information about the charging state through the first communication unit and the second communication unit, the functions performed by each of these first and second controllers thereof can also be variously distributed.

INDUSTRIAL APPLICABILITY

The present invention relates to a portable radiography device, and is applicable to a portable radiography device miniaturized to be suitable for intraoral radiography and the like in dental clinics, and a charging cradle including the same. In addition, the present invention is applicable to a portable radiography device for nondestructive testing of a system or equipment and a charging cradle including the same.

The invention claimed is:

1. A portable radiography device comprising:
a radiography device main body having a rechargeable battery;
a first communication unit provided in the main body, and configured to transmit battery charging state information;
a charging cradle configured to receive external power to supply charging power to the battery;
a second communication unit provided in the charging cradle, and configured to receive the battery charging state information from the first communication unit;
a display unit provided in the charging cradle, and configured to display the battery charging state information;
an input unit provided in at least one of the main body and the charging cradle, and configured to receive a radiographic mode setting input; and
a controller provided in at least one of the main body and the charging cradle, and configured to set differently intensity of X-rays or time of X-rays according to the radiographic mode.

2. The portable radiography device of claim 1, wherein the battery charging state information includes information on a possible number of times of radiography according to residual battery capacity.

3. The portable radiography device of claim 2, wherein the controller is further configured to calculate a real-time possible number of times of radiography by using real-time residual battery capacity detected in a predetermined time period and data on power consumption per one radiography prestored in a memory and provide the real-time possible number of times of radiography to at least one of the first communication unit and the second communication unit.

4. The portable radiography device of claim 3, wherein the controller calculates a real-time possible number of times of radiography corresponding to a radiographic mode set by input, by using data on power consumption per one radiography by radiographic mode stored in the memory.

5. The portable radiography device of claim 3, wherein the predetermined time period is a time period shorter than a time required to charge the power consumption per one radiography.

6. The portable radiography device of claim 1, wherein the battery charging state information includes a charging amount based on electric energy, charging ratio with respect to battery capacity, a charging time, or battery temperature information.

7. The portable radiography device of claim 6, further comprising:
- an input unit provided in at least one of the main body and the charging cradle, and configured to receive a charging mode setting input; and
- a controller provided in at least one of the main body and the charging cradle, and configured to update battery charging state information corresponding to a charging mode set by input in a predetermined time period and provide the battery charging state information.

8. The portable radiography device of claim 1, wherein either the first communication unit or the second communication unit is provided with a beacon communication module, and provides the charging state information or positional information of the main body to a registered mobile device within a beacon communication area provided by the beacon communication module.

9. The portable radiography device of claim 8, wherein the main body receives radiography information from the registered mobile device within a beacon communication area and sets a radiographic mode automatically.

* * * * *